United States Patent [19]
Sy

[11] Patent Number: 5,600,049
[45] Date of Patent: Feb. 4, 1997

[54] PROCESS FOR DEPROPANIZING BENZENE

[75] Inventor: Angel Sy, Katy, Tex.

[73] Assignee: Chemical Research & Licensing Company, Pasadena, Tex.

[21] Appl. No.: 456,693

[22] Filed: Jun. 1, 1995

[51] Int. Cl.$^6$ .............................. C07C 2/64; C07C 15/067
[52] U.S. Cl. .................... 585/450; 585/446; 585/802; 585/804; 203/21; 203/27; 203/DIG. 8
[58] Field of Search ...................... 585/446, 802, 585/804, 402, 450, 910; 203/21, 27, DIG. 8

[56] References Cited

U.S. PATENT DOCUMENTS

| 2,916,888 | 12/1959 | Cobb | 62/33 |
|---|---|---|---|
| 4,336,046 | 6/1982 | Schorre et al. | 62/28 |
| 4,555,311 | 11/1985 | Ward | 203/21 |
| 4,849,569 | 7/1989 | Smith | 585/446 |
| 4,950,834 | 8/1990 | Arganbright et al. | 585/446 |
| 5,019,669 | 5/1991 | Adams et al. | 585/446 |
| 5,043,506 | 8/1991 | Crossland | 585/449 |
| 5,055,627 | 10/1991 | Smith et al. | 585/467 |
| 5,080,871 | 1/1992 | Adams et al. | 422/187 |
| 5,086,193 | 2/1992 | Sy | 585/446 |
| 5,113,031 | 5/1992 | Sy | 585/467 |
| 5,176,883 | 1/1993 | Smith et al. | 422/211 |
| 5,215,725 | 6/1993 | Sy | 422/212 |
| 5,336,821 | 8/1994 | DeGraff et al. | 585/402 |

Primary Examiner—Asok Pal
Assistant Examiner—In Suk Bullock
Attorney, Agent, or Firm—Kenneth H. Johnson

[57] ABSTRACT

In the alkylation of benzene with propylene in a distillation column reactor to produce cumene the overheads from the distillation reactor are fed to a depropanizer where the unreacted benzene is separated from $C_3$'s. Liquid propylene feed for the distillation column reactor is vaporized by indirect heat exchange with the overheads from the depropanizer to condense the overheads, thereby reducing the pressure in the depropanizer below what would be normally achieved with conventional condensing systems.

9 Claims, 1 Drawing Sheet

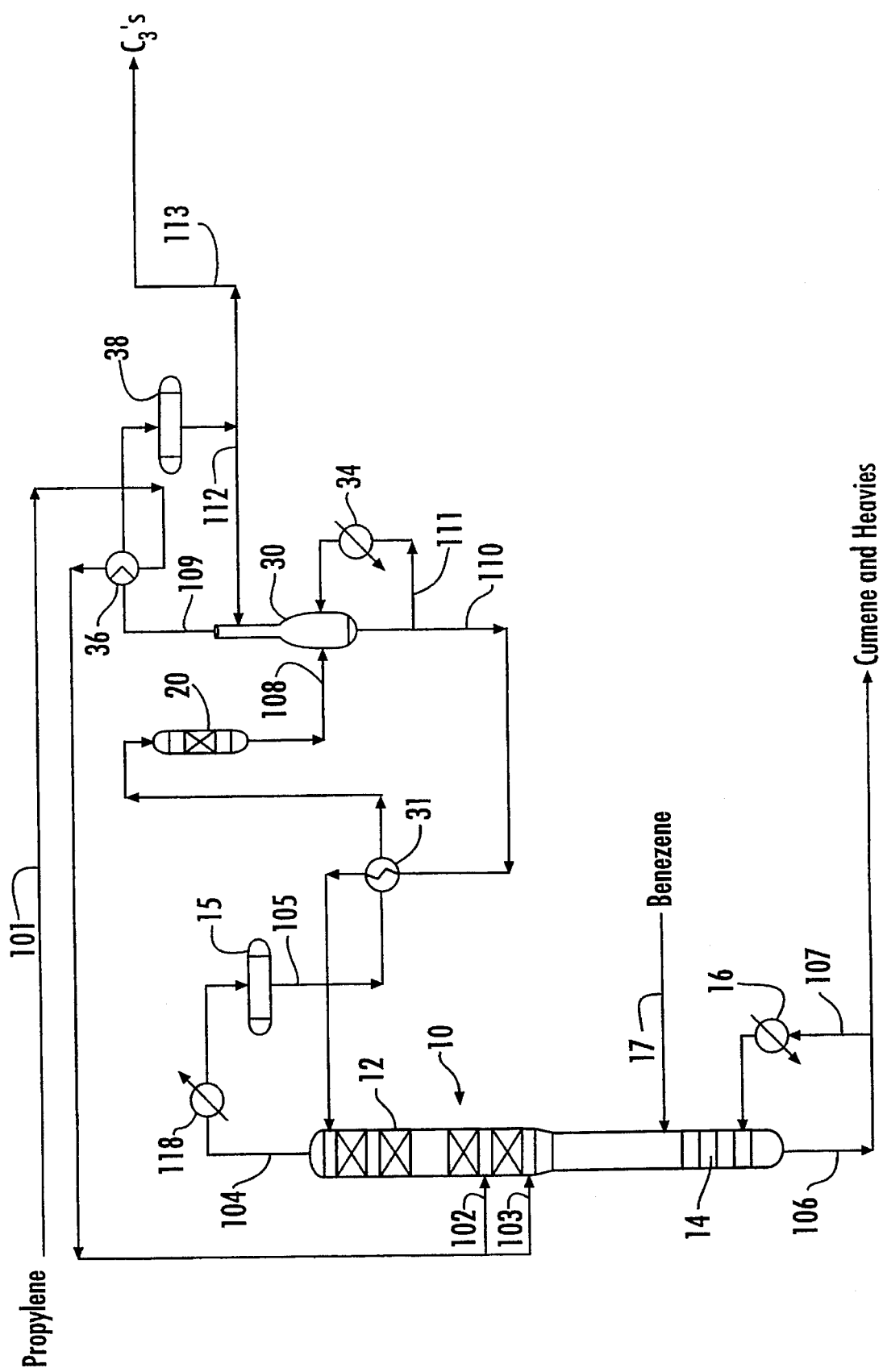

PROCESS FOR DEPROPANIZING BENZENE

BACKGROUND OF THE INVENTION

1. Field the Invention

The present invention relates to the depropanizing of unreacted benzene from the alkylation of benzene to produce cumene. More specifically the invention relates to the recovery of benzene from the overhead product of a distillation column reactor which produces cumene. In one embodiment the present invention relates to an integrated process for the production of cumene from the alkylation of benzene with propylene.

2. Related Information

Recently a new process has been developed for the production of cumene from the reaction of benzene and propylene. The new process utilizes a distillation column reactor to react benzene with propylene and simultaneously separate the higher boiling product cumene from unreacted benzene and $C_3$'s. In the preferred embodiment of the process the propylene, which is stored as a liquid, is vaporized and fed to the distillation column reactor as a gas to assure proper propylene/benzene mixing.

In the alkylation of benzene with an olefin in a distillation column reactor, the prior art shows the unreacted olefin (ethylene or propylene for example) being separated from the benzene in the overheads by partial condensation of the benzene and the use of a separator-reflux drum. See for example U.S. Pat. Nos. 4,849,569; 4,950,834; 5,019,669; 5,043,506; 5,055,627; 5,080,871; 5,086,193; 5,113,031; 5,176,883; 5,215,725; and 5,243,115 all commonly assigned.

Particularly in the alkylation of benzene with propylene it has been found to be more desirable to separate the unreacted $C_3$'s from the unreacted benzene by further fractional distillation in a depropanizer column.

The operating pressure of the depropanizer is dependent upon the temperature of the cooling medium in the overhead condenser. An advantage of the present invention is to obtain lower overhead temperatures which result in lower operating pressures in the depropanizer and thus lower heat requirements in the depropanizer reboiler. A further advantage is that the liquid propylene is vaporized as necessary for use in the alkylation with heat from the depropanization that would otherwise be wasted.

SUMMARY OF THE INVENTION

Briefly the invention is a process which utilizes the heat of vaporization of liquid propylene to cool the overheads from a benzene recovery column, wherein benzene containing dissolved $C_3$'s is distilled to remove the $C_3$'s as overheads. Liquid propylene is fed through the depropanizer condenser where it is vaporized by indirect heat exchange with the depropanizer overheads to cool and condense the overheads, whereby the depropanizer pressure is reduced by the refrigeration provided by the vaporized liquid propylene. The lower depropanizer pressure decreases the reboiler duty requirements and results in substantial improvement in the overall energy economy of the process. Using the present invention the heat of vaporization of the depropanizer is partially recovered and used to vaporize the liquid propylene from storage into the necessary vapor for the alkylation reaction. The typical improvement in the operating pressure in the depropanizer according to the present invention is about 60–120 psig compared to conventional water cooled condensers. Normally a water condenser would result in a pressure in the depropanizer in the range of 200 to 250 psig at temperatures in the range of 40° to 46° C. For example with the present invention the pressure would be reduced to about 135 psig at a temperature of 25° C., resulting in significant reduction in reboiler duty of 80 to 90% of original requirement. Generally the present invention will operate at pressures in the range of 80–190 psig more preferably 120 to 150 psig at temperatures in the range of 20° to 30° C.

In one embodiment the production of cumene is carried out by the reaction of benzene with propylene in a distillation column reactor where unreacted benzene in the overhead from the distillation column reactor is separated in a depropanizer distillation column. The vaporous propylene used to refrigerate the depropanizer is fed to the distillation column reactor below or along the catalyst bed or by prior blending with the benzene feed to the distillation reactor column.

BRIEF DESCRIPTION OF THE DRAWING

The FIGURE is a simplified flow diagram in schematic form showing one embodiment of the present invention.

DESCRIPTION OF THE PREFERRED EMBODIMENT

Benzene can be alkylated with propylene to produce cumene in a distillation column reactor containing a particulate acid alkylation catalyst prepared in the form of a catalytic distillation structure. Examples of the particulate acid alkylation catalyst include molecular sieves, zeolites and acidic ion exchange resins. Typically the distillation column reactor will contain an alkylation catalyst, such as a zeolite or molecular sieve, in the form of a catalytic distillation structure in the upper one-half to one-third of the column. The catalytic distillation structure acts as both catalyst and contact structure for the fractional distillation going on inside the column. The unreacted benzene and $C_3$'s are taken overhead and the alkylated product is taken as bottoms.

Generally the alkylated product also contains some poly-substituted aromatics such as poly-isopropyl benzene (PIPB) which can be recovered and transalkylated with benzene to additional cumene in a transalkylator with the product being fed back to the stripping section of the distillation column reactor for separation from unreacted benzene.

The particulate acid alkylation catalysts may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

Any of the now extensive types of catalytic distillation structures are suitable for use herein, such as, that described in detail in U.S. Pat. No. 4,215,011, incorporated herein and which comprises placing the mole sieve or cation exchange resin particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

Other suitable catalytic distillation structures are disclosed in U.S. Pat. Nos. 4,443,559, 5,057,468, 5,189,001, 5,262,012, 5,266,546, 5,348,710, U.S. Ser. No. 08/188,803 filed Jan. 31, 1994 (docket 1373) and U.S. Pat. No. 5,073, 236 each of which is incorporated herein.

Typical conditions for the reaction include from about 20 to 120 psig distillation column pressure and catalyst bed temperatures of from about 200° to 350° F. Benzene is generally provided in molar excess to the propylene in a ratio of from 5:1 to 100:1.

At the reaction conditions some poly-substituted benzene is also produced which includes some poly-isopropyl benzene (PIPB). The PIPB and heavier are separated from the cumene in a distillation column and then the PIPB further separated from the heavies and transalkylated with benzene in a fixed bed reactor utilizing the same or same type catalyst as in the distillation column reactor.

Referring now to the FIGURE there is shown a simplified flow diagram in schematic form of the preferred embodiment of the invention.

The distillation column reactor is shown at 10 having catalyst beds in the rectification section 12 and standard trays in the stripping section 14. Propylene is fed via line 101 and vaporized in heat exchanger 36 before being split into feed lines 102 and 103. Benzene is fed via flow line 117 to the stripping section 14 of the distillation column reactor 10 where the excess benzene is stripped upward into the reaction zone and the cumene removed as product. Unreacted benzene and $C_3$'s are taken over head via flow line 104 and condensed in heat exchanger 118 with the liquids collected in receiver 15. The liquids from the receiver are preheated in heat exchanger 31 and fed via flow line 105 to finishing reactor 20 where substantially all of the unreacted propylene is reacted. The effluent from the finishing reactor 20 is fed via flow line 108 to depropanizer column 30 where the unreacted $C_3$'s (mostly propane) are separated from the unreacted benzene which is taken via flow line 110 and cooled in heat exchanger 31 prior to being recycled to the distillation column reactor 10 as reflux. A portion of the benzene from the bottoms of the depropanizer is passed via 111 through reboiler 34 to provide heat to the column 30.

The overheads from the depropanizer are taken via flow line 109 and condensed by indirect heat exchange with the liquid propylene feed in heat exchanger 36. The liquid propylene is vaporized in its side of the heat exchanger 36 while providing excellent cooling of the depropanizer overheads. The condensed overheads, mainly propane, are collected in receiver 38 where some is returned as reflux via flow line 112 and the remainder removed via flow line 113 for recovery or other disposal.

The bottoms from the distillation column reactor 10 contain the product cumene and also some poly substituted benzenes such as poly-isopropyl benzene. These bottoms are removed via flow line 106 and passed to recovery section (not shown) where cumene is separated by distillation from polyalkylated benzene. A portion of the bottoms are passed through reboiler 16 via flow line 107 to provide heat to the distillation column reactor. Make up benzene to the distillation column reactor is thus provided as excess benzene to the transalkylator.

The catalyst used in all three reactors may be identical with only that in the distillation column reactor having to be in the form of a catalytic distillation structure.

The invention claimed is:

1. A process which utilizes the heat of vaporization of liquid propylene to cool the overheads from a benzene recovery column, comprising fractionally distilling benzene containing dissolved $C_3$'s in a distillation column to vaporize and remove the $C_3$'s as overheads, contacting said vaporized $C_3$'s by indirect heat exchange with liquid propylene in a condenser where said liquid propylene is vaporized and the overheads are cooled and condensed, whereby the distillation column pressure is reduced by the refrigeration provided by the vaporized liquid propylene.

2. In a process for the production of cumene by the reaction of benzene with propylene and concurrent separation of the product in a distillation column reactor having a propylene feed to said distillation column reactor and the subsequent separation of unreacted $C_3$'s from unreacted benzene in a depropanizer column, wherein the improvement comprising vaporizing the propylene feed by indirect heat exchange with the depropanizer column overheads.

3. A process for the production of cumene comprising the steps of:
   (a) feeding (1) a first stream containing benzene and (2) a second stream containing propylene to a distillation column reactor;
   concurrently in said distillation column reactor
      (i) contacting said benzene and propylene in a reaction distillation zone in the presence of an acidic alkylation catalyst prepared in the form of a catalytic distillation structure to react a portion of said benzene with a portion of said propylene to form a reaction mixture containing product cumene, unreacted benzene and unreacted propylene and $C_3$'s, and
      (ii) separating the product cumene from the unreacted benzene, unreacted propylene and $C_3$'s by fractional distillation;
   (b) removing the cumene product from said distillation column reactor as bottoms;
   (c) removing the unreacted benzene, unreacted propylene and $C_3$'s from said distillation column reactor as overheads;
   (d) separating the unreacted benzene from the unreacted propylene and $C_3$'s by fractional distillation in a depropanizer whereby the unreacted propylene and $C_3$'s are taken as overheads and the unreacted benzene is taken as bottoms; and
   (e) condensing the overheads containing the unreacted propylene and $C_3$'s by indirect heat exchange with said second stream thereby vaporizing said second stream prior to feeding said second stream to said distillation column reactor.

4. The process according to claim 3 wherein said unreacted benzene is cooled and returned to said distillation column reactor as reflux.

5. The process according to claim 3 wherein poly substituted benzenes are also produced and are withdrawn as bottoms along with said cumene.

6. The process according to claim 5 wherein said poly substituted benzenes are separated from said cumene.

7. The process according to claim 3 wherein said depropanizer operates at pressures in range of 80–190 psig at temperatures in the range of 20° to 30° C.

8. The process according to claim 3 wherein said depropanizer operates at pressures in the range of 120 to 150 psig.

9. The process according to claim 8 wherein said second stream is fed to said distillation column reactor at two points along said distillation column reactor.

* * * * *